(12) United States Patent
Kim et al.

(10) Patent No.: US 10,962,466 B2
(45) Date of Patent: Mar. 30, 2021

(54) PARTICULATE MATTERS SENSOR DEVICE AND MANUFACTURING METHOD OF SENSOR UNIT PROVIDED IN THIS

(71) Applicants: Hyundai Motor Company, Seoul (KR); Kia Motors Corporation, Seoul (KR)

(72) Inventors: Dong Gu Kim, Suwon-si (KR); Sang Hyeok Yang, Suwon-si (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 168 days.

(21) Appl. No.: 16/201,752

(22) Filed: Nov. 27, 2018

(65) Prior Publication Data

US 2019/0137379 A1 May 9, 2019

Related U.S. Application Data

(62) Division of application No. 15/372,297, filed on Dec. 7, 2016, now abandoned.

(30) Foreign Application Priority Data

Sep. 12, 2016 (KR) .................... 10-2016-0117548

(51) Int. Cl.
*G01N 15/10* (2006.01)
*H05K 3/46* (2006.01)
*F01N 13/00* (2010.01)
*G01N 15/06* (2006.01)
*G01N 27/02* (2006.01)
*F01N 11/00* (2006.01)
(Continued)

(52) U.S. Cl.
CPC ......... *G01N 15/1031* (2013.01); *F01N 11/00* (2013.01); *F01N 13/008* (2013.01); *G01K 7/00* (2013.01); *G01N 15/0606* (2013.01); *G01N 15/0656* (2013.01); *G01N 27/02* (2013.01); *G01N 27/028* (2013.01); *G01N 33/0027* (2013.01); *H05K 3/4602* (2013.01); *F01N 2560/05* (2013.01); *F01N 2560/20* (2013.01); *F01N 2900/14* (2013.01); *G01N 2015/0046* (2013.01)

(58) Field of Classification Search
None
See application file for complete search history.

(56) References Cited

U.S. PATENT DOCUMENTS 4,540,479 A 9/1985 Sakurai
4,656,832 A 4/1987 Yukihisa
(Continued)

FOREIGN PATENT DOCUMENTS

CN 102272571 A 12/2011
CN 103776752 A 5/2014
(Continued)

*Primary Examiner* — Harshad R Patel
*Assistant Examiner* — Nigel H Plumb
(74) *Attorney, Agent, or Firm* — Morgan, Lewis & Bockius LLP (57) ABSTRACT

Disclosed is a particulate matters sensor device detecting particulate matters (PM) included in exhaust gas, including: a detecting device having detecting electrodes formed on an external peripheral surface of a base having a bar shape with a circular cross section at a predetermined interval in a predetermined direction to sense the particulate matters included in the exhaust gas.

4 Claims, 7 Drawing Sheets

(51) Int. Cl.
  *G01K 7/00* (2006.01)
  *G01N 33/00* (2006.01)
  *G01N 15/00* (2006.01)

(56) References Cited

U.S. PATENT DOCUMENTS

| | | |
|---|---|---|
| 5,247,827 A | 9/1993 | Shah |
| 8,578,756 B2 | 11/2013 | Suzuki |
| 9,897,528 B2 | 2/2018 | Motomura |
| 2006/0107730 A1 | 5/2006 | Schumann |
| 2008/0282769 A1 | 11/2008 | Nelson |
| 2009/0113983 A1 | 5/2009 | Krafthefer |
| 2009/0309571 A1 | 12/2009 | Katsuyama |
| 2010/0107737 A1 | 5/2010 | Krafthefer |
| 2010/0126248 A1 | 5/2010 | Hall |
| 2010/0264025 A1 | 10/2010 | Nair |
| 2011/0252865 A1 | 10/2011 | Tokuda |
| 2011/0259079 A1 | 10/2011 | Maeda |
| 2012/0073267 A1 | 3/2012 | Cook |
| 2012/0103057 A1 | 5/2012 | Kimata |
| 2012/0103059 A1 | 5/2012 | Kimata |
| 2012/0151992 A1 | 6/2012 | Harada |
| 2013/0030678 A1 | 1/2013 | Aoki |
| 2013/0219990 A1 | 8/2013 | Allmendinger |
| 2014/0116113 A1 | 5/2014 | Lee |
| 2015/0300919 A1 | 10/2015 | Ante |
| 2016/0238547 A1 | 8/2016 | Park |
| 2017/0226916 A1 | 8/2017 | Zhang |
| 2017/0261417 A1 | 9/2017 | Zhang |
| 2017/0307498 A1 | 10/2017 | Sugiyama |
| 2018/0100423 A1 | 4/2018 | Zhang |
| 2018/0156709 A1 | 6/2018 | Kim |

FOREIGN PATENT DOCUMENTS

| | | |
|---|---|---|
| CN | 105301071 A | 2/2016 |
| CN | 107167402 A | 9/2017 |
| JP | 2002-131278 A | 5/2002 |
| JP | 2011-247650 A | 12/2011 |
| JP | 2016-161542 A | 9/2016 |
| KR | 10-2012-0076797 A | 7/2012 |

PARTICULATE MATTERS SENSOR DEVICE AND MANUFACTURING METHOD OF SENSOR UNIT PROVIDED IN THIS

CROSS-REFERENCE TO RELATED APPLICATION

The present application is a Divisional of U.S. patent application Ser. No. 15/372,297, filed Dec. 7, 2016, which claims priority to Korean Patent Application No. 10-2016-0117548 filed on Sep. 12, 2016, the entire contents of which applications are incorporated herein for all purposes by these references.

BACKGROUND OF THE INVENTION

Field of the Invention

The present invention relates to a particulate matters sensor device including a sensing unit which precisely senses particulate matters included in exhaust gas and a manufacturing method of a sensor unit provided in this.

Description of Related Art

A diesel particulate filter for reducing particulates is applied to diesel vehicles and a differential pressure sensor is adopted to sense the quantity of particulates collected in the diesel particulate filter (DPF).

In the future, it may be impossible to prevent the diesel particulate filter from being damaged and precision deteriorates by using the existing differential pressure sensor according to an exhaust gas regulation.

Figure 7:
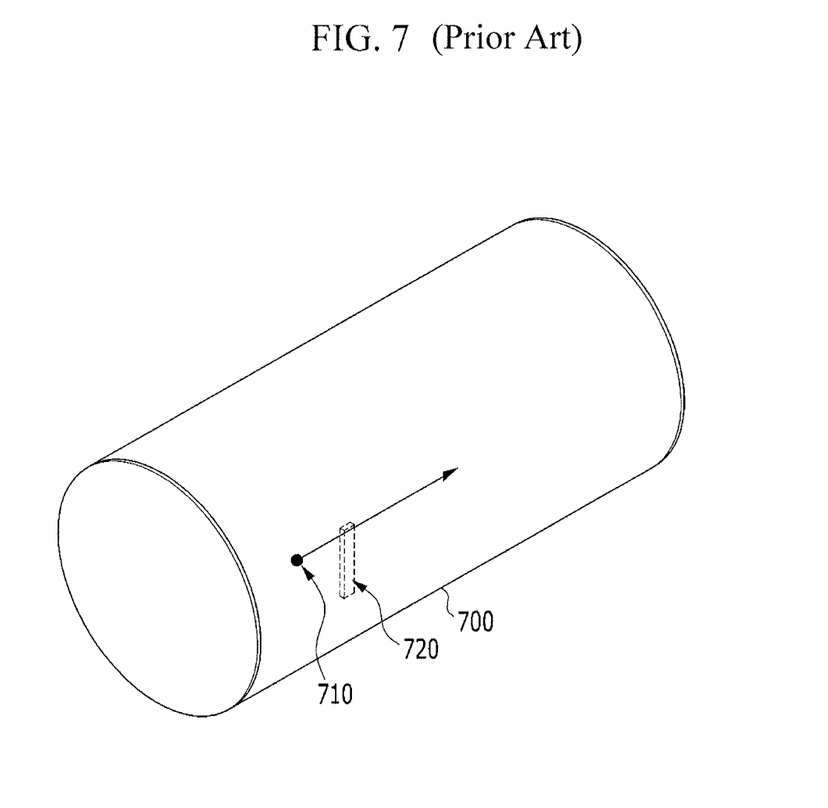
FIG. 7 is a schematic configuration diagram of a general exhaust line.

FIG. 7 is a schematic configuration diagram of a general exhaust line.

Referring to FIG. 7, exhaust gas flows in the exhaust line 700 and particulate matters 710 are included in the exhaust gas.

The particulate matters 710 pass adjacent to a particulate matters (PM) sensor 720 and as the particulate matters 710 pass, the PM sensor 720 generates a signal.

The signal generated by the PM sensor 720 is generated due to electric charges induced to the PM sensor 720 when charged particulate matters pass.

Meanwhile, sensitivity of the sensor deteriorates according to an installation direction of the PM sensor and the sensitivity of the sensor deteriorates according to a flow direction of the exhaust gas. Therefore, a research for solving the problems has been progressed. Moreover, a research into a manufacturing method for the PM sensor to achieve such a purpose has been simultaneously progressed.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Various aspects of the present invention are directed to providing a particulate matters sensor device which stably and accurately detects particulate matters included in exhaust gas regardless of an installation direction and a manufacturing method of a sensor device provided in this.

Various aspects of the present invention are directed to providing a particulate matters sensor device detecting particulate matters (PM) included in exhaust gas, including a detecting device having detecting electrodes formed on an external peripheral surface of a base having a bar shape with a circular cross section at a predetermined interval in a predetermined direction to sense the particulate matters included in the exhaust gas.

The detecting electrodes may be formed in a flow direction of the exhaust gas.

A temperature electrode configured to sense a temperature and a heating electrode configured to generate heat may be formed in the base based on the detecting electrodes.

The particulate matters sensor device may further include a first tube into which the detecting device is inserted in a longitudinal direction, and a first passage through which the exhaust gas is discharged may be formed at an end portion corresponding to an end portion of the detecting device and a second passage through which the exhaust gas flows from the external surface to the internal surface of the first tube at an opposite side to the first passage based on the detecting electrode may be formed.

The particulate matters sensor device may further include a second tube having an internal peripheral surface corresponding to the external peripheral surface of the first tube, and a third tube through which the exhaust gas flows in from the outside to the inside may be formed on an end surface of the second tube.

The detecting electrodes may be formed in the longitudinal direction of the base.

The particulate matters sensor device may further include the first tube into which the detecting device is inserted in the longitudinal direction, and the first and second passages through which the exhaust gas flows in or out may be formed at least at both sides of a position corresponding to the detecting electrode in the first tube and the guides which guide the exhaust gas passing through the first and second passages to flow on the circumference of the detecting device may be formed on the internal surface of the first tube.

The detecting electrodes may be formed in the circumferential direction of the base.

The particulate matters sensor device may further include the first tube into which the detecting device is inserted in the longitudinal direction, and the first passage through which the exhaust gas is discharged may be formed at the end portion corresponding to the end portion of the detecting device and the second passage through which the exhaust gas flows from the external surface to the internal surface of the first tube at the opposite side to the first passage based on the detecting electrode may be formed, and the guides may be formed on the internal surface of the second passage so that the exhaust gas is discharged through the first passage while rotating along the external peripheral surface of the detecting device.

The detecting electrodes may be formed in a screw shape to rotate along the external peripheral surface of the detecting device from the first passage to the second passage.

Various aspects of the present invention are directed to providing a manufacturing method of a detecting device, including: preparing a base having a shape corresponding to an external peripheral surface of a cylinder; preparing a sheet in which detecting electrodes detecting particulate matters extend in a predetermined direction at a predetermined interval; attaching the sheet onto the external peripheral surface of the base; and sintering the sheet at a predetermined temperature to fix the sheet to the base.

The method may further include: forming a temperature electrode for detecting a temperature on the sheet; and forming a heating electrode on the sheet, and the detecting electrodes may be formed on the temperature electrode or the heating electrode and the detecting electrodes may be exposed to the outside.

The detecting electrodes may extend in the longitudinal direction of the base and be arrayed at a predetermined interval in the circumferential direction of the base.

The detecting electrodes may extend in the circumferential direction of the base and be arrayed at a predetermined interval in the longitudinal direction of the base.

The detecting electrodes may be formed to have a screw shape on the external peripheral surface of the detecting device.

The detecting electrode may include one of jewelry materials and the base and the sheet may include one of ceramic materials.

The detecting electrode may include at least one of W, MO, and Pt and the base and the base and the sheet may include one of $Al_2O_3$, Zirconia, AlN, and SiN.

According to exemplary embodiments of the present invention, sensitivity can be enhanced by increasing a detecting area of a detecting electrode and detecting precision of the detecting electrode can be enhanced regardless of an installation direction of the detecting device.

The methods and apparatuses of the present invention have other features and advantages which will be apparent from or are set forth in more detail in the accompanying drawings, which are incorporated herein, and the following Detailed Description, which together serve to explain certain principles of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Hereinafter, an exemplary embodiment of the present invention will be described in detail with reference to the accompanying drawings.

However, since size and thickness of each component illustrated in the drawings are arbitrarily represented for convenience in explanation, the present invention is not particularly limited to the illustrated size and thickness of each component and the thickness is enlarged and illustrated to clearly express various parts and areas.

However, parts not associated with description are omitted for clearly describing the exemplary embodiment of the present invention and like reference numerals designate like elements throughout the specification.

In the following description, names of components, which are in the same relationship, are divided into "the first", "the second", and the like to distinguish the components, but the present invention is not limited to the order.

Figure 1:
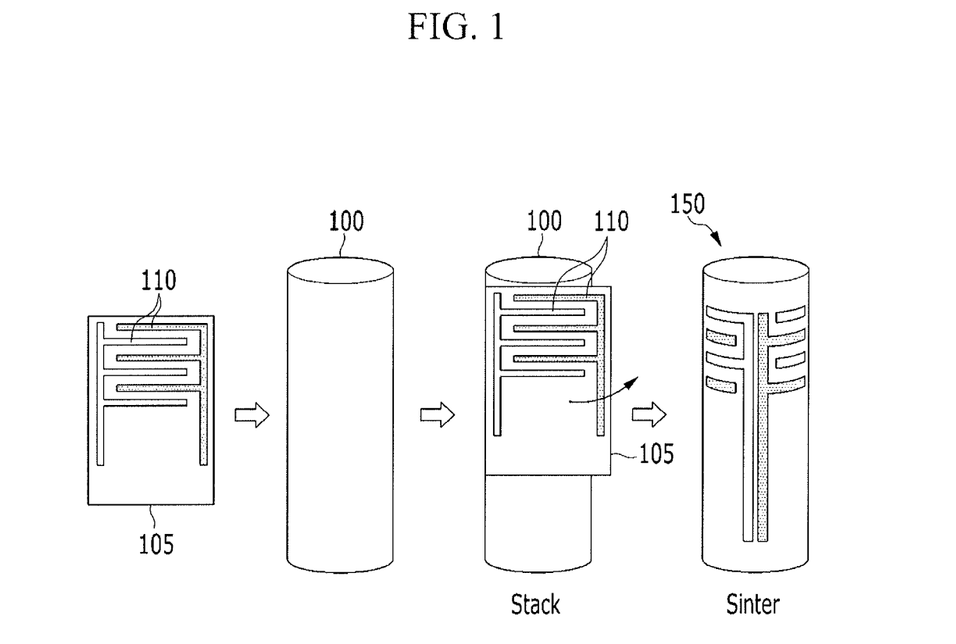
FIG. 1 is a schematic configuration diagram illustrating a manufacturing order of a detecting device according to an exemplary embodiment of the present invention.

FIG. 1 is a schematic configuration diagram illustrating a manufacturing order of a detecting device according to an exemplary embodiment of the present invention.

Referring to FIG. 1, a detecting electrode 110 is formed along a line set on a ceramic sheet 105. The detecting electrode 110 includes a cathode line and an anode lie and in the detecting electrode 110, the cathode line and the anode line are alternately arrayed at a predetermined interval.

Prior art is referred for a method of forming the detecting electrode 110 on the ceramic sheet 105 and detailed description thereof is omitted.

In addition, the base 100 has a cylindrical shape (alternatively, a bar shape) in which a cross section is circular and the sheet 105 in which the detecting electrode 110 is formed is sequentially attached onto an external peripheral surface of the base 100. In addition, the ceramic sheet 105 is sintered at a predetermined temperature to be fixed to the base 100.

Figure 2:
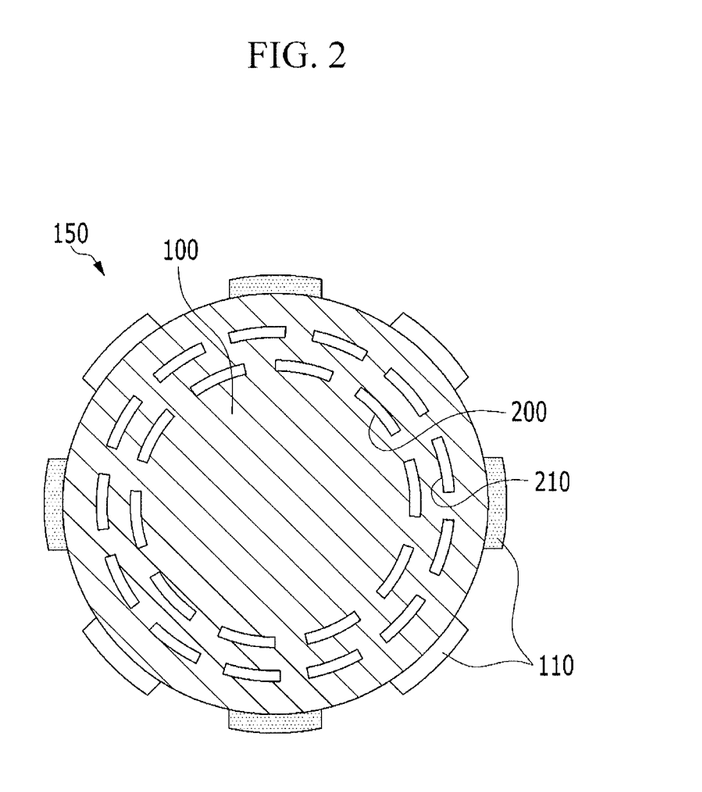
FIG. 2 is a schematic cross-sectional view illustrating a cross section of the detecting device according to the exemplary embodiment of the present invention.

FIG. 2 is a schematic cross-sectional view illustrating a cross section of the detecting device according to the exemplary embodiment of the present invention.

Referring to FIG. 2, the detecting electrode 110 is formed outside the detecting device 150, a temperature electrode 210 is formed inside the detecting electrode 110, and a heating electrode is formed inside the temperature electrode 210.

In the exemplary embodiment of the present invention, the heating electrode 200 may be formed on the sheet 105, the temperature electrode 210 may be formed thereon, and the detecting electrode 110 may be formed thereon.

In addition, the sheet 105 in which the heating electrode 200, the temperature electrode 210, and the detecting electrode 110 are sequentially stacked may be attached onto the external peripheral surface of the base 100.

Figure 3:
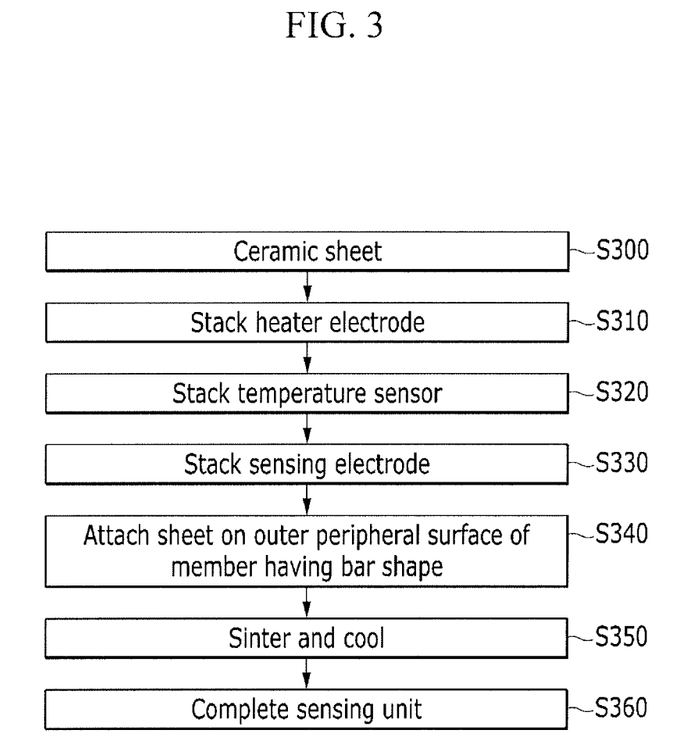
FIG. 3 is a flowchart of a manufacturing method of a detecting device according to an exemplary embodiment of the present invention.

FIG. 3 is a flowchart of a manufacturing method of a detecting device according to another exemplary embodiment of the present invention.

Referring to FIG. 3, in S300, the ceramic sheet 105 is prepared and in S310, the heating electrode 200 is stacked on the ceramic sheet 105.

In S320, the temperature electrode 210 is stacked on the heating electrode 200 and in S330, the detecting electrode 110 is stacked. Herein, the temperature electrode 210 and the heating electrode 200 may be selectively adopted.

In addition, in S340, the heating electrode 200, the temperature electrode 210, and the detecting electrode 110 are attached onto the external peripheral surface of the base 100 having the bar shape with the circular cross section, in S350, the sheet 105 is sintered at a predetermined temperature to be fixed to the base 100, and in S360, the detecting device 150 is completed.

Figure 4:
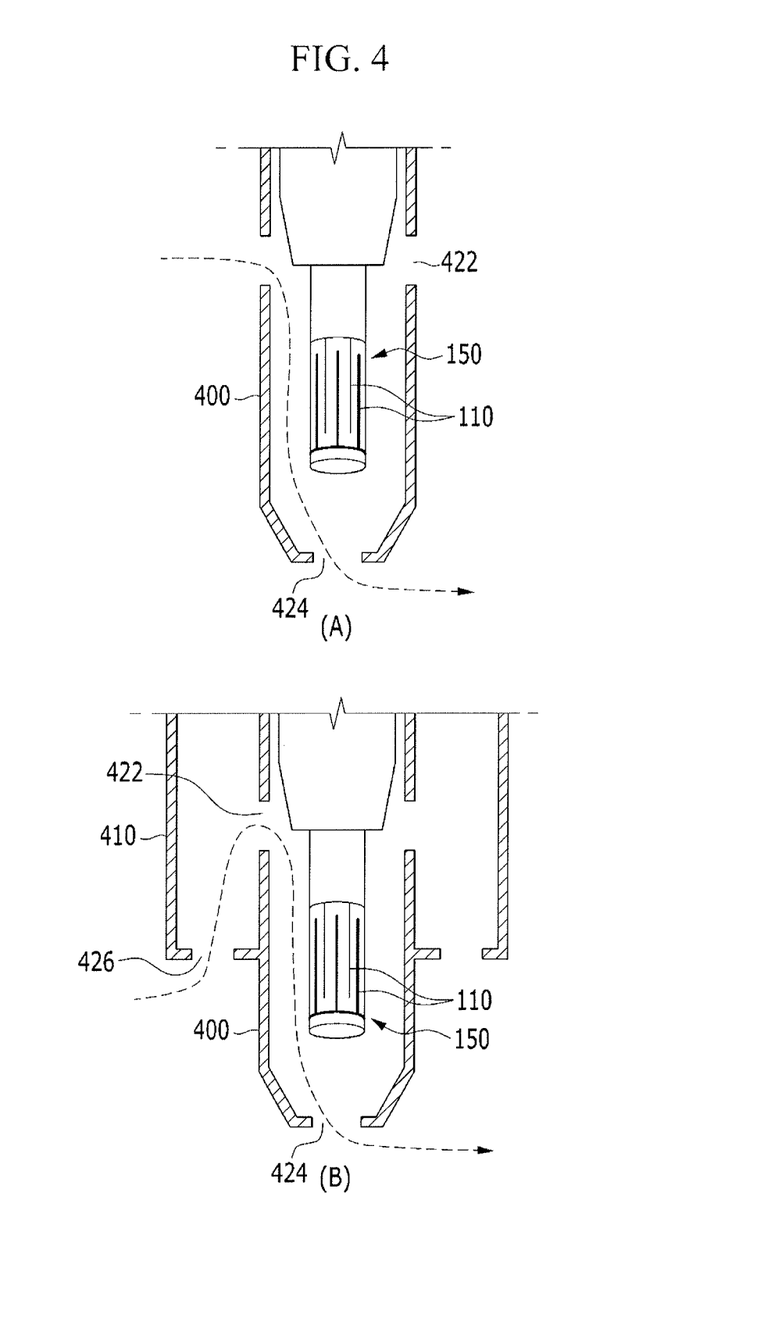
FIG. 4 is a cross-sectional view of a particulate matters sensor device including a detecting device according to the exemplary embodiment of the present invention.

FIG. 4 is a cross-sectional view of a particulate matters sensor device including a detecting device according to the exemplary embodiment of the present invention.

Referring to FIG. 4A, a first tube 400 is disposed and the detecting device 150 is inserted into the first tube 400 in a longitudinal direction. Herein, the external peripheral surface of the detecting device 150 and the internal peripheral surface of the first tube 400 are formed at a predetermined interval from each other.

A first passage 424 through which exhaust gas is discharged is formed at the center of the bottom of the first tube 400 and a second passage 422 is formed from one internal surface to one external surface of the first tube 400 at an opposite side to the first passage 424 based on the detecting electrode 110.

The exhaust gas is supplied to the inside of the first tube 400 through the second passage 422, and the exhaust gas which enters the inside of the first tube 400 moves down and is discharged down through the first passage 424.

Herein, the detecting electrode 110 of the detecting device 150 detects particulate matters (PM) included in the exhaust gas. In addition, the cathode line and the anode line of the detecting electrode 110 extend in the longitudinal direction of the detecting device 150 and are arrayed at a predetermined interval in a circumferential direction.

Referring to FIG. 4B, the first tube 400 is inserted into a second tube 410 and the detecting device 150 is inserted into the first tube 400 in the longitudinal direction.

Herein, the external peripheral surface of the detecting device 150 and the internal peripheral surface of the first tube 400 are formed at a predetermined interval from each other.

The first passage 424 through which the exhaust gas is discharged is formed at the center of the bottom of the first tube 400 and the second passage 422 is formed from one internal surface to one external surface of the first tube 400 at the opposite side to the first passage 424 based on the detecting electrode 110.

In addition, a third passage 426 through which the exhaust gas flows in is formed on the bottom of the second tube 410. Accordingly, the exhaust gas is supplied to the inside of the second tube 410 through the third passage 426 and supplied to the inside of the first tube 400 through the second passage 422, and the exhaust gas which enters the inside of the first tube 400 moves down.

Herein, the detecting electrode 110 of the detecting device 150 detects the particulate matters (PM) included in the exhaust gas and the exhaust gas is discharged down through the first passage 424.

As illustrated in FIG. 4, the cathode line and the anode line of the detecting electrode 110 extend in the longitudinal direction of the detecting device 150 and are arrayed at a predetermined interval in the circumferential direction.

Figure 5:
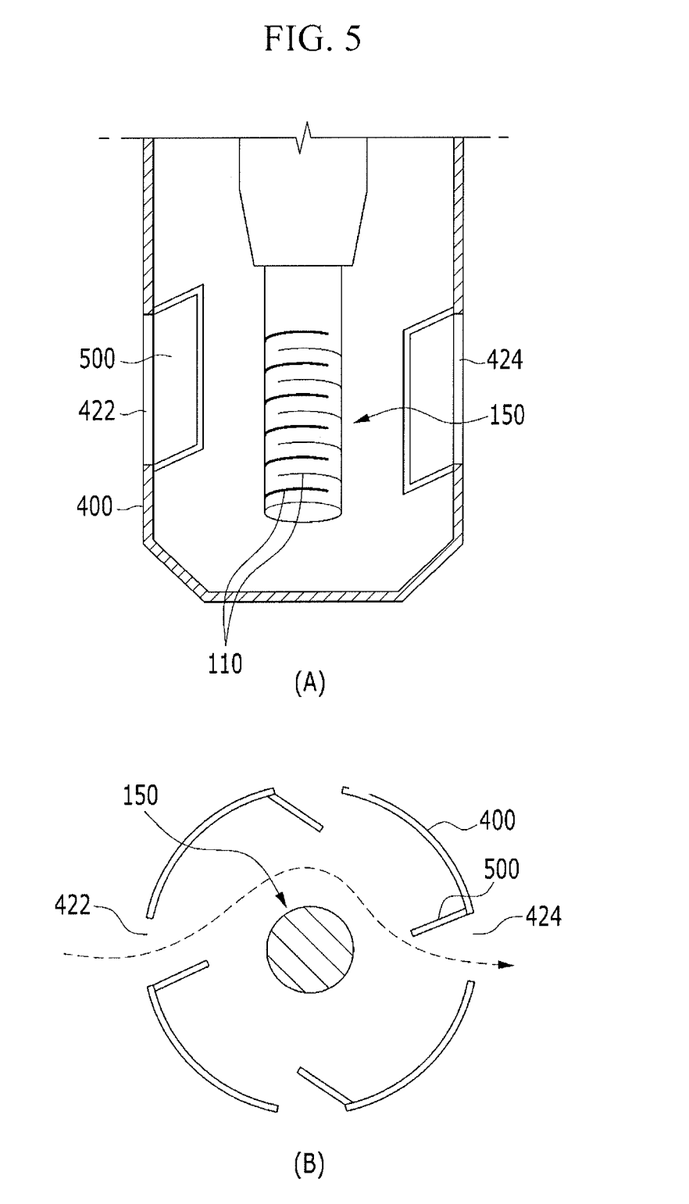
FIG. 5 is a cross-sectional view of a particulate matters sensor device including a detecting device according to another exemplary embodiment of the present invention.

FIG. 5 is a cross-sectional view of a particulate matters sensor device including a detecting device according to another exemplary embodiment of the present invention.

Referring to FIG. 5A, the first tube 400 is disposed and the detecting device 150 is inserted into the first tube 400 in the longitudinal direction. Herein, the external peripheral surface of the detecting device 150 and the internal peripheral surface of the first tube 400 are formed at a predetermined interval from each other.

The first passage 424 is formed from one internal surface to one external surface of the first tube 400, the second passage 422 is formed from the other internal surface to the other external surface, and the first passage 424 and the second passage 424 are formed at positions corresponding to the detecting electrode 110 of the detecting device 150.

Accordingly, the exhaust gas which enters the inside of the first tube 400 through the second passage 422 is discharged through the first passage 424 by passing through the periphery of the detecting device 150.

In the exemplary embodiment of the present invention, guides 500 are formed on one side and the other side of the internal surface of the first tube 400 and the guides 500 control the flow direction of the exhaust gas which flows in through the second passage 422 to allow the exhaust gas to flow onto one external peripheral surface of the detecting device 150.

Further, the guides 500 guide the flow of the exhaust gas so that the exhaust gas is easily discharged through the first passage 424. Moreover, the first passage 424 and the second passage 422 may be formed at a predetermined interval along the circumference of the first tube 400.

As illustrated in FIG. 5, the cathode line and the anode line of the detecting electrode 110 extend in the circumferential direction of the detecting device 150 and are arrayed at a predetermined interval in the longitudinal direction.

Figure 6:
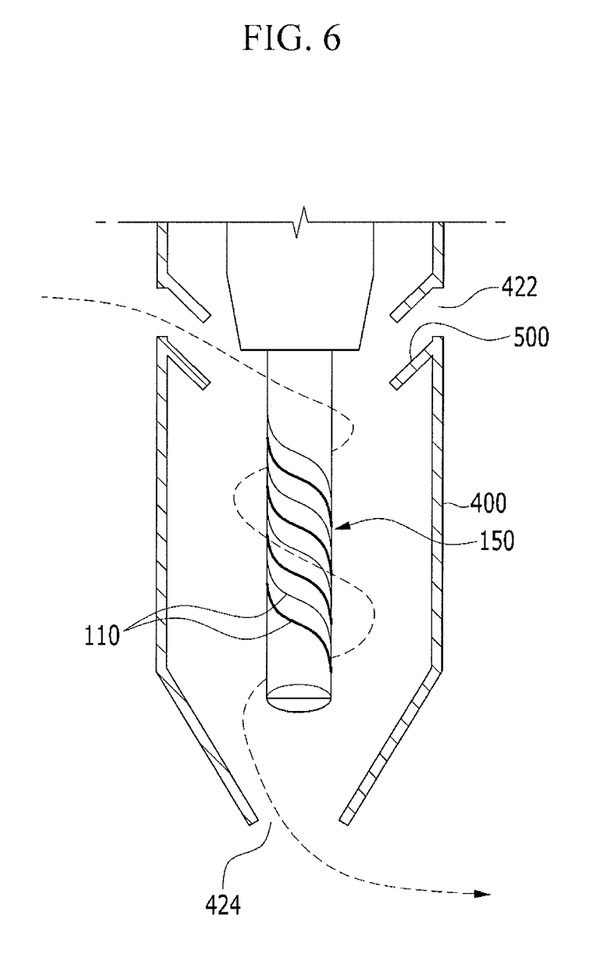
FIG. 6 is a cross-sectional view of a particulate matters sensor device including a detecting device according to yet another exemplary embodiment of the present invention.

FIG. 6 is a cross-sectional view of a particulate matters sensor device including a detecting device according to yet another exemplary embodiment of the present invention.

Referring to FIG. 6, the first tube 400 is disposed and the detecting device 150 is inserted into the first tube 400 in the longitudinal direction. Herein, the external peripheral surface of the detecting device 150 and the internal peripheral surface of the first tube 400 are formed at a predetermined interval from each other.

The first passage 424 through which the exhaust gas is discharged is formed at the center of the bottom of the first tube 400 and the second passage 422 is formed from one internal surface to one external surface of the first tube 400 at the opposite side to the first passage 424 based on the detecting electrode 110.

The exhaust gas is supplied to the inside of the first tube 400 through the second passage 422 and the exhaust gas which enters the inside of the first tube 400 moves down.

In addition, the detecting electrode 110 detects the particulate matters (PM) included in the exhaust gas and the exhaust gas is discharged down through the first passage 424.

Meanwhile, the guides 500 which moves the exhaust gas down while rotating the exhaust gas are formed to extend on the internal surface of the first tube 400 in the second passage 422.

The exhaust gas which enters the inside of the first tube 400 through the second passage 422 moves down while rotating in a screw shape along the external peripheral surface of the detecting device 150 and the internal peripheral surface of the first tube 400 to be discharged down through the first passage 424.

As illustrated in FIG. 6, the cathode line and the anode line of the detecting electrode 110 extend in the screw shape from the top portion to the bottom on the external peripheral surface of the detecting device 150 in a movement direction of the exhaust gas.

In addition, the second passage 422 may be formed on the circumference of the first tube 400 at a predetermined interval or consecutively formed within a predetermined angle range.

In the exemplary embodiment of the present invention, the detecting electrode may include one of jewelry materials and the base and the sheet may include one of ceramic materials.

In addition, the detecting electrode may include at least one of W, MO, and Pt and the base and the sheet may include one of $Al_2O_3$, Zirconia, AIN, and SiN.

While this invention has been described in connection with what is presently considered to be practical example embodiments, it is to be understood that the invention is not limited to the disclosed exemplary embodiments. On the contrary, it is intended to cover various modifications and equivalent claims as well as various alternatives and modifications thereof. It is intended that the scope of the invention be defined by the Claims appended hereto and their equivalents."

For convenience in explanation and accurate definition in the appended claims, the terms "upper", "lower", "inner", "outer", "up", "down", "upper", "lower", "upwards", "downwards", "front", "rear", "back", "inside", "outside", "inwardly", "outwardly", "interior", "exterior", "inner", "outer", "forwards", and "backwards" are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A particulate matters sensor device detecting particulate matters (PM) included in exhaust gas, comprising: a detecting device having detecting electrodes formed on an external peripheral surface of a base having a bar shape with a circular cross section at a predetermined interval in a predetermined direction to sense the particulate matters included in the exhaust gas; and a first tube into which the detecting device is inserted in a longitudinal direction of the detecting device, wherein: the detecting electrodes are formed in a flow direction of the exhaust gas, a first passage through which the exhaust gas is discharged is formed at an end portion thereof corresponding to an end portion of the detecting device and a second passage through which the exhaust gas flows from an external surface to an internal surface of the first tube at an opposite side to the first passage based on the detecting electrodes is formed, the first and second passages are formed at least at a first side and a second side of a position corresponding to the detecting electrodes in the first tube, and guides which guide the exhaust gas passing through the first and second passages to flow on an external circumference of the detecting device are formed on the internal surface of the first tube, wherein a cathode line and an anode line of the detecting device are formed on an external surface of the detecting device to extend in the longitudinal direction of the detecting device on the external surface of the detecting device and are arrayed at a predetermined interval in a circumferential direction of the detecting device, and wherein the exhaust gas is supplied to the inside of the first tube through the second passage, and the exhaust gas which enters the inside of the first tube moves down and is discharged down through the first passage.

2. The particulate matters sensor device of claim 1, wherein the detecting electrodes are formed in a circumferential direction of the base.

3. A particulate matters sensor device detecting particulate matters (PM) included in exhaust gas, comprising: a detecting device having detecting electrodes formed on an external peripheral surface of a base having a bar shape with a circular cross section at a predetermined interval in a predetermined direction to sense the particulate matters included in the exhaust gas; and a first tube into which the detecting device is inserted in a longitudinal direction of the detecting device, wherein: the detecting electrodes are formed in a flow direction of the exhaust gas, a first passage through which the exhaust gas is discharged is formed at an end portion corresponding to an end portion of the detecting device and a second passage through which the exhaust gas flows from an external surface to an internal surface of the first tube at an opposite side to the first passage based on the detecting electrode is formed, and guides are formed on an internal surface of the second passage wherein the exhaust gas is discharged through the first passage while rotating along an external peripheral surface of the detecting device, wherein a cathode line and an anode line of the detecting device are formed on an external surface of the detecting device to extend in the longitudinal direction of the detecting device on the external surface of the detecting device and are arrayed at a predetermined interval in a circumferential direction of the detecting device, and wherein the exhaust gas is supplied to the inside of the first tube through the second passage, and the exhaust gas which enters the inside of the first tube moves down and is discharged down through the first passage.

4. The particulate matters sensor device of claim 3, wherein
   the detecting electrodes are formed in a screw shape to rotate along the external peripheral surface of the detecting device from the first passage to the second passage.

\* \* \* \* \*